（12）United States Patent
Wiklander et al.

(10) Patent No.: US 11,975,070 B2
(45) Date of Patent: May 7, 2024

(54) AFFINITY PURIFICATION OF ENGINEERED EXTRACELLULAR VESICLES

(71) Applicant: Evox Therapeutics Ltd, Oxford (GB)

(72) Inventors: Oscar Wiklander, Solna (SE); Andre Gorgens, Huddinge (SE)

(73) Assignee: Evox Therapeutics Ltd, Oxford (GB)

( * ) Notice: Subject to any disclaimer, the term of this patent is extended or adjusted under 35 U.S.C. 154(b) by 989 days.

(21) Appl. No.: 16/756,785

(22) PCT Filed: Oct. 23, 2018

(86) PCT No.: PCT/EP2018/078976
§ 371 (c)(1),
(2) Date: Apr. 16, 2020

(87) PCT Pub. No.: WO2019/081474
PCT Pub. Date: May 2, 2019

(65) Prior Publication Data
US 2021/0188903 A1 Jun. 24, 2021

(30) Foreign Application Priority Data
Oct. 24, 2017 (GB) ..................................... 1717446

(51) Int. Cl.
| A61K 39/395 | (2006.01) |
| A61K 35/55 | (2015.01) |
| B01D 15/38 | (2006.01) |
| C07K 14/70 | (2006.01) |
| C07K 14/705 | (2006.01) |
| C07K 14/71 | (2006.01) |
| C07K 14/715 | (2006.01) |

(52) U.S. Cl.
CPC ............ *A61K 39/395* (2013.01); *A61K 35/55* (2013.01); *B01D 15/3809* (2013.01); *C07K 14/70596* (2013.01); *C07K 14/7151* (2013.01); *C07K 2319/30* (2013.01); *C07K 2319/705* (2013.01)

(58) Field of Classification Search
CPC ...... A61K 35/55; A61K 39/395; A61K 47/06; B01D 15/3809; C07K 14/70596; C07K 14/7151; C07K 2319/30; C07K 2319/705
See application file for complete search history.

(56) References Cited

U.S. PATENT DOCUMENTS

| 11,236,143 | B2 * | 2/2022 | Wiklander | ............ | C07K 14/705 |
| 2012/0207754 | A1 | 8/2012 | Giacalone et al. | | |
| 2015/0018241 | A1 * | 1/2015 | Falkenstein | ........ | G01N 33/6854 |
| | | | | | 530/387.3 |
| 2016/0223441 | A1 | 8/2016 | Gjerde | | |
| 2020/0109183 | A1 * | 4/2020 | Wiklander | ......... | A61K 47/6913 |
| 2022/0098267 | A1 * | 3/2022 | Wiklander | ......... | A61K 47/6901 |

FOREIGN PATENT DOCUMENTS

| CN | 1325441 | A | | 12/2001 | | |
| CN | 1345328 | A | | 4/2002 | | |
| CN | 102811782 | A | | 12/2012 | | |
| CN | 104619388 | A | | 5/2015 | | |
| GB | 2044775 | A | * | 10/1980 | ........... | C07K 16/065 |
| JP | 2014506893 | A | | 3/2014 | | |
| JP | 2015533490 | A | | 11/2015 | | |
| WO | WO 00/44389 | A2 | | 8/2000 | | |
| WO | WO-2011110515 | A1 | | 9/2011 | | |
| WO | WO 2014/168548 | A2 | | 10/2014 | | |
| WO | WO-2016017037 | A1 | | 2/2016 | | |
| WO | WO 2018/015535 | A1 | | 1/2018 | | |

OTHER PUBLICATIONS

Nizard et al. "Anchoring antibodies to membranes using a diphtheria toxin T domain-ZZ fusion protein as a pH sensitive membrane anchor", FEBS Letters, 1998, vol. 433, p. 83-88.
Mathivanan S. et al. "ExoCarta 2012: database of exosomal proteins, RNA and lipids", Nucleic Acids Research, 2012, vol. 40, p. D1241-D1244.

* cited by examiner

*Primary Examiner* — John Kim
(74) *Attorney, Agent, or Firm* — COOLEY LLP; Matthew Pavao

(57) ABSTRACT

The present invention pertains to affinity chromatography isolation and purification of extracellular vesicles (EVs). The EVs of the present invention are engineered to enable highly specific binding to e.g. chromatography matrices, which is highly useful for affinity-based isolation and purification of EVs from complex biological fluids such as cell culture medium or biological fluids.

10 Claims, 6 Drawing Sheets

AFFINITY PURIFICATION OF ENGINEERED EXTRACELLULAR VESICLES

CROSS-REFERENCE TO RELATED APPLICATIONS

This application is a national stage application, filed under 35 U.S.C. 371, of International Application No. PCT/EP2018/078976, filed Oct. 23, 2018, which claims priority to, and the benefit of, GB 1717446.7, filed Oct. 24, 2017, the contents of each of which are herein incorporated by reference in their entirety.

TECHNICAL FIELD

The present invention pertains to affinity chromatography isolation and purification of extracellular vesicles (EVs) therapeutics, wherein the EVs are engineered to enable highly specific binding to e.g. chromatography matrices and optionally subsequent elution.

BACKGROUND ART

Extracellular vesicles (EVs) are nano-sized vesicles (generally less than 1000 nm in hydrodynamic diameter) that are released by EV-producing cells into the extracellular environment. EVs and in particular exosomes (which or often defined by different parameters, e.g. a hydrodynamic radius of between 30 and 120 nm and the presence of various tetraspanin proteins in their membrane) have been shown to be able to transport protein biologics, such as antibodies and decoy receptors, into target cells, enabling an entirely novel form of advanced biological therapeutics harnessing the properties of EVs in combination with the specificity of recombinant proteins.

Conventional methods to prepare and isolate EVs (e.g. exosomes) involve a series of differential centrifugation steps to separate the vesicles from cells or cell debris present in the culture medium into which the EVs are released by EV-producing cells. Typically, series of centrifugations at e.g. 300 g, 10,000 g and 70,000 g or 100,000 g are applied, upon which the resulting pellet at the bottom of the tube is resuspended to a fraction of its original volume with a saline solution to constitute a concentrated EV or exosome solution. However, these methods are essentially unsuitable for clinical applications for a number of reasons: (1) the extended length of time needed for the entire process, (2) issues around scale-up and validation in a GMP environment, (3) significant risk of contamination by cell debris, (4) poor reproducibility due to operator variability, (5) aggregation of EVs/exosomes resulting from pelleting of the vesicles, (6) low recovery at end of processing, and (7) negative impact on vesicle morphology and thereby biodistribution and activity. There is therefore a need for improved methods of preparing membrane vesicles, suitable with industrial constraints and allowing production of vesicle preparations of therapeutic quality. To that end, PCT application WO2000/044389 discloses methods for preparing membrane vesicles from biological samples through chromatographic techniques, such as anion exchange chromatography and/or gel permeation chromatography. WO2014/168548 discloses a significantly improved isolation and purification method for EVs, namely the use of sequential combinations of filtration and various forms of liquid chromatography, for instance a combination of ultrafiltration and size-exclusion liquid chromatography. However, there is room for significant improvement over said disclosures, especially as the EV therapeutics field advances toward clinical translation and impact of EV-based therapies.

SUMMARY OF THE INVENTION

It is hence an object of the present invention to overcome the above-identified problems associated with the isolation and purification of EVs. Furthermore, the present invention aims to satisfy other existing needs within the art, for instance to develop generally applicable affinity purification strategies for EV purification at high yields and with high specificity. In particular the previously known methods for purifying exosomes are not ideally suited to large scale production and scale up that would be necessary for commercial production of EV therapeutics. The present invention allows much larger scale purification of engineered exosomes with high affinity than would be achievable with previously known methods.

The present invention achieves these and other objectives by utilizing chromatography matrices comprising Fc domains, to which EVs engineered to comprise Fc binding polypeptides are being attached. As such, the present invention thus relates to various aspects and embodiments surrounding processes for isolating and/or purifying EVs, typically comprising the steps of (i) contacting a medium comprising the EVs with a chromatography matrix comprising Fc domains, (ii) allowing the EVs to adsorb to the Fc domains, and (iii) eluting the EVs by passing across the chromatography matrix a medium that releases the EVs from the Fc domains. As above-mentioned, the EVs of present invention are engineered to comprise and typically display on their surface Fc binding polypeptides such as Protein A, Protein G, Protein A/G, Z domain, ZZ domain (two operably linked copies of the Z domain), human FCGRI, human FCGRIIA, human FCGRIIB, human FCGRIIC, human FCGRIIIA, human FCGR3B, human FCAMR, human FCERA, human FCAR, mouse FCGRI, mouse FCGRIIB, mouse FCGRIII, mouse FCGRIV, mouse FCGRn, and various combinations, derivatives, or alternatives thereof.

In a further aspect, the present invention relates the use of a chromatography matrix for binding to EVs, wherein the chromatography matrix comprises Fc domains. In yet further aspects, the present invention relates to EVs comprising at least one Fc binding polypeptide, wherein said EVs are obtainable via capture or isolation using the purification/isolation methods of the present invention. Furthermore, the present invention also relates to EVs comprising at least one fusion protein, wherein the at least one fusion protein comprises at least one Fc binding polypeptide fused to at least one exosomal polypeptide, which are highly useful as a platform to enable purification of EVs for instance for therapeutic application.

Finally, the present invention also relates to fusion proteins comprising at least one Fc binding polypeptide (also referred to as Fc binder) and at least one exosomal polypeptide, and polynucleotide constructs encoding for such fusion proteins, as well as vectors, EVs and cells comprising such constructs.

DETAILED DESCRIPTION OF THE INVENTION

Figure 1:
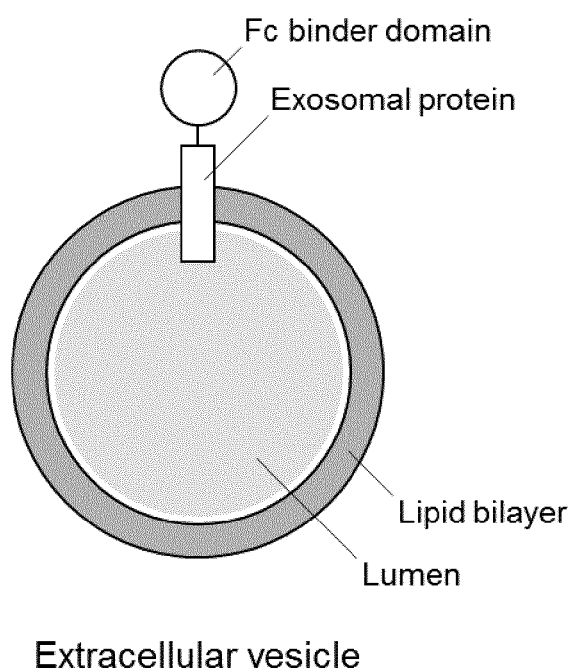
FIG. 1. Schematic illustration of an EV comprising a fusion protein comprising an exosomal protein fused to an Fc binding polypeptide (i.e. the Fc binder domain). The Fc binder is capable of binding e.g. an antibody and/or any other protein comprising an Fc domain, thereby turning the EV into a multivalent delivery vehicle for protein therapeutics.

The present invention relates to affinity purification and/or isolation of EVs, utilizing EV engineering strategies to enable specific, high-throughput isolation of pure batches of EVs for various applications, typically within EV-based therapy.

For convenience and clarity, certain terms employed herein are collected and described below. Unless otherwise defined, all technical and scientific terms used herein have the same meaning as commonly understood by one of ordinary skill in the art to which this invention belongs.

Where features, aspects, embodiments, or alternatives of the present invention are described in terms of Markush groups, a person skilled in the art will recognize that the invention is also thereby described in terms of any individual member or subgroup of members of the Markush group. The person skilled in the art will further recognize that the invention is also thereby described in terms of any combination of individual members or subgroups of members of Markush groups. Additionally, it should be noted that embodiments and features described in connection with one of the aspects and/or embodiments of the present invention also apply mutatis mutandis to all the other aspects and/or embodiments of the invention. For example, the Fc domains described herein shall be understood to be disclosed also as parts of antibodies of any type that comprises such Fc domains. Furthermore, EVs comprising Fc binding polypeptides as described herein shall be shall be understood to additionally further comprise various therapeutic agents, such as nucleic acid based agents, protein and/or peptide based agents, small molecule agents, and any combinations thereof. Furthermore, all polypeptides and proteins identified herein can be freely combined in fusion proteins using conventional strategies for fusing polypeptides. As a non-limiting example, all Fc binding polypeptides described herein may be freely combined in any combination with one or more exosomal polypeptides. Also, Fc binding polypeptides may be combined with each other to generate constructs comprising more than one Fc binding polypeptide. Moreover, any and all features (for instance any and all members of a Markush group) can be freely combined with any and all other features (for instance any and all members of any other Markush group), e.g. any EV comprising an Fc binding protein may be purified and/or isolation using any Fc domain containing protein, such as any antibody or other Fc domain containing protein. Furthermore, when teachings herein refer to EVs (and/or the EVs comprising Fc binding polypeptides) in singular and/or to EVs as discrete natural nanoparticle-like vesicles it should be understood that all such teachings are equally relevant for and applicable to a plurality of EVs and populations of EVs. As a general remark, the Fc binding polypeptides, the Fc domain containing proteins such as the antibodies, the EV-producing cell sources, the exosomal proteins, and all other aspects, embodiments, and alternatives in accordance with the present invention may be freely combined in any and all possible combinations without deviating from the scope and the gist of the invention. Furthermore, any polypeptide or polynucleotide or any polypeptide or polynucleotide sequences (amino acid sequences or nucleotide sequences, respectively) of the present invention may deviate considerably from the original polypeptides, polynucleotides and sequences as long as any given molecule retains the ability to carry out the desired technical effect associated therewith. As long as their biological properties are maintained the polypeptide and/or polynucleotide sequences according to the present application may deviate with as much as 50% (calculated using for instance BLAST or ClustalW) as compared to the native sequence, although a sequence identity that is as high as possible is preferable (for instance 60%, 70%, 80%, or e.g. 90% or higher). For instance, the combination (fusion) of e.g. at least one Fc binding polypeptide and at least one exosomal protein implies that certain segments of the respective polypeptides may be replaced and/or modified and/or that the sequences may be interrupted by insertion of other amino acid stretches, meaning that the deviation from the native sequence may be considerable as long as the key properties (e.g. Fc binding properties, trafficking to the surface of exosomes, therapeutic activity, etc.) are conserved. Similar reasoning thus naturally applies to the polynucleotide sequences encoding for such polypeptides. All accession numbers and SEQ ID NOs mentioned herein in connection with peptides, polypeptides and proteins shall only be seen as examples and for information only, and all peptides, polypeptides and proteins shall be given their ordinary meaning as the skilled person would understand them. Thus, as above-mentioned, the skilled person will also understand that the present invention encompasses not merely the specific SEQ ID NOs and/or accession numbers that may be referred to herein but also variants and derivatives thereof. All accession numbers referred to herein are UniProtKB accession numbers as per the 24 Oct. 2017 version of the database, and all proteins, polypeptides, peptides, nucleotides and polynucleotides mentioned herein are to be construed according to their conventional meaning as understood by a skilled person.

The terms "extracellular vesicle" or "EV" or "exosome" are used interchangeably herein and shall be understood to relate to any type of vesicle that is obtainable from a cell in any form, for instance a microvesicle (e.g. any vesicle shed from the plasma membrane of a cell), an exosome (e.g. any vesicle derived from the endo-lysosomal pathway), an apoptotic body (e.g. obtainable from apoptotic cells), a microparticle (which may be derived from e.g. platelets), an ectosome (derivable from e.g. neutrophils and monocytes in serum), prostatosome (e.g. obtainable from prostate cancer cells), or a cardiosome (e.g. derivable from cardiac cells), etc. The sizes of EVs may vary considerably but an EV typically has a nano-sized hydrodynamic radius, i.e. a radius below 1000 nm. Exosomes represent a particularly advantageous category of EVs and typically have a hydrodynamic radius of around 30 to 150 nm. Clearly, EVs may be derived from any cell type, both in vivo, ex vivo, and in vitro. Furthermore, the said terms shall also be understood to relate to extracellular vesicle mimics, cell membrane-based vesicles obtained through for instance membrane extrusion, sonication, or other techniques, etc. In preferred embodiments, the EVs of the present invention are of eukaryotic origin, even more preferably of mammalian origin, meaning that they are obtained from eukaryotic and/or mammalian cell sources. It will be clear to the skilled artisan that when describing medical and scientific uses and applications of the EVs, the present invention normally relates to a plurality of EVs, i.e. a population of EVs which may comprise thousands, millions, billions or even trillions of EVs. As can be seen from the experimental section below, EVs may be present in concentrations such as $10^5$, $10^8$, $10^{10}$, $10^{11}$, $10^{12}$, $10^{13}$, $10^{14}$, $10^{15}$, $10^{18}$, $10^{25}$, $10^{30}$ EVs (often termed "particles") per unit of volume (for instance per ml), or any other number larger, smaller or anywhere in between. In the same vein, the term "population", which may e.g. relate to an EV comprising a certain fusion protein between an exosomal polypeptide and an Fc binding polypeptide which in turn may be bound to an Fc containing protein of interest (which may be present on a chromatography matrix), shall be understood to encompass a plurality of entities constituting such a population. In other words, individual EVs when present in a plurality constitute an EV population. Thus, naturally, the present invention pertains both to individual EVs and populations comprising EVs, as will be clear to the skilled person. The dosages of EVs when applied in vivo may naturally vary considerably depending on the disease to be treated, the administration route, any targeting moieties present on the EVs, the pharmaceutical formulation, etc. Furthermore, the EVs of the present invention may also comprise additional therapeutic agents. In some embodiments, the additional therapeutic agent may be at least one therapeutic small molecule drug. In some embodiments, the therapeutic small molecule drug may be selected from the group consisting of DNA damaging agents, agents that inhibit DNA synthesis, microtubule and tubulin binding agents, anti-metabolites, inducers of oxidative damage, anti-angiogenics, endocrine therapies, anti-estrogens, immuno-modulators such as Toll-like receptor agonists or antagonists, histone deacetylase inhibitors, inhibitors of signal transduction such as inhibitors of kinases, inhibitors of heat shock proteins, retinoids, inhibitors of growth factor receptors, anti-mitotic compounds, anti-inflammatories, cell cycle regulators, transcription factor inhibitors, and apoptosis inducers, and any combination thereof. In further embodiments, the additional therapeutic agent may be a therapeutic nucleic acid-based agent. Such nucleic acid-based therapeutic agents may be selected from the group comprising single-stranded RNA or DNA, double-stranded RNA or DNA, oligonucleotides such as sRNA, splice-switching RNA, CRISPR guide strands, short hairpin RNA (shRNA), miRNA, antisense oligonucleotides, polynucleotides such as mRNA, plasmids, or any other RNA or DNA vector. Of particular interest are nucleic acid-based agents which are chemically synthesized and/or which comprise chemically modified nucleotides such as 2'-O-Me, 2'-O-Allyl, 2'-O-MOE, 2'-F, 2'-CE, 2'-EA 2'-FANA, LNA, CLNA, ENA, PNA, phosphorothioates, tricyclo-DNA, etc. In yet further embodiments, the EVs as per the present invention may comprise additional therapeutic agents which may be protein and/or peptides. Such proteins and/or peptides may be present inside of the EVs, inserted into the EV membrane or in association with the EV membrane, protruding from the EV into the extravesicular environment and/or coated onto the EV surfaces. Such therapeutic protein and/or peptide agents may be selected from a group of non-limiting examples including: antibodies such as monoclonal or polyclonal antibodies, intrabodies, single chain variable fragments (scFv), affibodies, bi- and multispecific antibodies or binders, affibodies, darpins, receptors, ligands, enzymes for e.g. enzyme replacement therapy or gene editing, tumor suppressors, viral or bacterial inhibitors, cell component proteins, DNA and/or RNA binding proteins, DNA repair inhibitors, nucleases, proteinases, integrases, transcription factors, growth factors, apoptosis inhibitors and inducers, toxins (for instance *pseudomonas* exotoxins), structural proteins, neurotrophic factors such as NT3/4, brain-derived neurotrophic factor (BDNF) and nerve growth factor (NGF) and its individual subunits such as the 2.5S beta subunit, ion channels, membrane transporters, proteostasis factors, proteins involved in cellular signaling, translation- and transcription related proteins, nucleotide binding proteins, protein binding proteins, lipid binding proteins, glycosaminoglycans (GAGs) and GAG-binding proteins, metabolic proteins, cellular stress regulating proteins, inflammation and immune system regulating proteins, mitochondrial proteins, and heat shock proteins, etc. In a preferred embodiment, the therapeutic agent may be a CRISPR-associated (Cas) polypeptide (such as Cas9 (as a non-limiting example the accession number Q99ZW2)) with intact nuclease activity which is associated with (i.e. carries with it) an RNA strand that enables the Cas polypeptide to carry out its nuclease activity in a target cell once delivered by the EV. Alternatively, in another preferred embodiment, the Cas polypeptide may be catalytically inactive, to enable targeted genetic engineering. Yet another alternative may be any other type of CRISPR effector such as the single RNA-guided endonuclease Cpf1 (from species such as Acidaminococcus or Lachnospiraceae) (as non-limiting examples the accession numbers U2UMQ6 and A0Q7Q2). Additional preferred embodiments include therapeutic proteins selected from the group comprising enzymes for lysosomal storage disorders, for instance glucocerebrosidases such as imiglucerase, alpha-galactosidase, alpha-L-iduronidase, iduronate-2-sulfatase and idursulfase, arylsulfatase, galsulfase, acid-alpha glucosidase, sphingomyelinase, galactocerebrosidase, galactosylceramidase, glucosylceramidase (as a non-limiting example the accession number P04062) ceramidase, alpha-N-acetylgalactosaminidase, beta-galactosidase, lysosomal acid lipase, acid sphingomyelinase, NPC1 (as a non-limiting example the accession number O15118), NPC2 (as a non-limiting example the accession number P61916), heparan sulfamidase, N-acetylglucosaminidase, heparan-α-glucosaminide-N-acetyltransferase, N-acetylglucosamine 6-sulfatase, galactose-6-sulfate sulfatase, galactose-6-sulfate sulfatase, hyaluronidase, alpha-N-acetyl neuraminidase, GlcNAc phosphotransferase, mucolipin1, palmitoyl-protein thioesterase, tripeptidyl peptidase I, palmitoyl-protein thioesterase 1, tripeptidyl peptidase 1, battenin, linclin, alpha-D-mannosidase, beta-mannosidase, aspartylglucosaminidase, alpha-L-fucosidase, cystinosin, cathepsin K, sialin, LAM P2, and hexoaminidase. In other preferred embodiments, the therapeutic protein may be e.g. an intracellular protein that modifies inflammatory responses, for instance epigenetic proteins such as methylases and bromodomains, or an intracellular protein that modifies muscle function, e.g. transcription factors such as MyoD (as a non-limiting example the accession number P15172) or Myf5, proteins regulating muscle contractility e.g. myosin, actin, calcium/binding proteins such as troponin, or structural proteins such as dystrophin (as a non-limiting example the accession number P11532), mini dystrophin (as a non-limiting example the accession number P15172), utrophin, titin, nebulin, dystrophin-associated proteins such as dystrobrevin, syntrophin, syncoilin, desmin, sarcoglycan, dystroglycan, sarcospan, agrin, and/or fukutin. Yet another non-limiting strategy which may be utilized to improve intracellular bioactivity of an EV-delivered therapeutic agent include designing EVs comprising endosomal escape peptides or proteins, such as HA2, cell-penetrating peptides (CPPs) such as the TAT peptide, transportan, penetratin, poly-lysine, or gp41, cholera toxin, Shiga toxin, saporin, diphtheria toxin peptides, etc. Displaying such endosomal escape domains on the surface of an EV may enhance both internalization into target cells and subsequent endosomal escape.

The terms "antibody" and "mAb" and "Ab" as described herein is to be understood to include both antibodies in their entirety (i.e. whole antibodies) and any derivatives thereof. Conventionally, an antibody refers to a glycoprotein comprising at least two heavy (H) chains and two light (L) chains inter-connected by disulfide bonds, or an antigen binding-portion thereof. Each heavy chain is comprised of a heavy chain variable region (abbreviated herein as VH) and a heavy chain constant region. Each light chain is comprised of a light chain variable region (abbreviated herein as VL) and a light chain constant region. The variable regions of the heavy and light chains contain a binding domain that interacts with an antigen. The VH and VL regions can be further subdivided into regions of hypervariability, termed complementarity determining regions (CDR), interspersed with regions that are more conserved, termed framework regions (FR). Importantly, for the purposes of the present invention an antibody of interest preferably has an Fc domain or a derivative thereof to which the Fc binding polypeptides of the present invention can bind, in order to enable binding and/or capturing of the EVs. Antibodies of use in the invention may be monoclonal antibodies (mAbs) or polyclonal antibodies. Antibodies of particular utility in the invention may be chimeric antibodies, CDR-grafted antibodies, nanobodies, human or humanised antibodies or any derivative thereof as long as it can be bound by the Fc binding polypeptide, to enable purification/isolation of the Fc binding polypeptide EVs as per the present invention. The production of antibodies is generally outside of the scope of the present invention but typically both monoclonal and polyclonal antibodies are raised experimental non-human mammals such as goat, rabbit, llama, camelids, rat or mouse, but suitable antibodies may also be the result of other production methodologies, e.g. the standard somatic cell hybridization technique of Kohler and Milstein. Hybridoma production in e.g. the mouse is a very well-established procedure and can be achieved using techniques well known in the art. An antibody of use in the invention may be a human antibody, humanized antibody, and/or any type of chimeric antibody. The term "human antibody", as used herein, is intended to include antibodies having variable regions in which both the framework and CDR regions are derived from human germline immunoglobulin sequences. The human antibodies of use in the invention may include amino acid residues not encoded by human germline immunoglobulin sequences (e.g., mutations introduced by random or site-specific mutagenesis in vitro or by somatic mutation in vivo). The term "antibody derivatives" refers to any modified form of an antibody, e.g. an antibody having an amino acid sequence that is modified in any way, or a conjugate of the antibody and another agent or antibody, bispecific antibodies, multispecific antibodies, antibody domains, single-chain variable fragment (scFVs), single-domain antibodies, nanobodies, alphabodies, etc. The term "humanized antibody" refers to antibodies in which CDR sequences derived from another mammalian species, such as a mouse, camelid, llama, etc., have been grafted onto human framework sequences. Additional framework region modifications may be made within the human framework sequences. Antibodies in accordance with the present invention may include all isotypes and subtypes such as IgG (for instance IgG1, IgG2, IgG3, IgG4, IgG2a, IgG2d, and IgG2c), IgA, IgM, IgM, IgD, etc., and monomers, dimers, and oligomers thereof.

The terms "Fc containing protein" and "protein comprising an Fc domain" and "Fc domain-containing protein" and "Fc domain containing protein" and "Fc domain protein" and similar terms are used interchangeably herein and shall be understood to relate to any protein, polypeptide, or peptide (i.e. any molecule comprising a sequence of amino acids) which comprises at least one Fc domain, either naturally or as a result of engineering of the protein in question to introduce an Fc domain. Fc stands for "fragment crystallizable", which is the name of the tail regions of antibodies. Fc domains can however also be created and used on other proteins, not only antibodies. Non-limiting examples of such Fc domain-containing proteins include antibodies and antibody derivatives, Fc domain-containing bi- and multi-specific binders, any type of Fc domain-containing receptors or ligands, etc. Suitable Fc domains (which may be fused with a protein of interest natively lacking an Fc domain) include the following non-limiting examples: human IGHM, human IGHA1, human IGHA2, human IGKC, human IGHG1, human IGHG2, human IGHG3, human IGHG4, human IGHD, human IGHE, and any domains, derivatives, or combinations thereof. In essence, any protein of interest may be modified to incorporate an Fc domain as long as the binding between the Fc binding polypeptide of the EVs and the Fc domain is sufficiently strong and/or specific to enable purification and/or isolation of the EV, e.g. from a biological fluid such as a cell culture medium.

The Fc containing proteins (e.g. IgG antibodies) are often described herein as being "attached to" a chromatography matrix and/or any other type of so called solid-phase in a separation apparatus. Alternatively, EVs are sometimes referred to having "bound to their surface" or "attached to their surface" the Fc containing proteins, e.g. Fc domains of an antibody. These terms shall be understood in the context of the conventional interaction between an Fc binding polypeptide and an Fc domain, that is that the two polypeptides are interacting with each other in a way that results in a chemical bond (typically a non-covalent bond) forming between the Fc binding polypeptide and the Fc domain. Thus, this normally means that the EV which comprises the Fc binding polypeptide therefore has attached to it, by virtue of such a bond, the Fc domain of the Fc containing protein. As will be understood by the skilled person, an EV may consequently have a plurality of such Fc containing proteins bound (attached) to it, enabling the chemical interaction to serve as a basis for affinity purification of EVs from a medium such as a biological fluid or a cell culture medium.

The terms "Fc binding polypeptide" and "Fc binding protein" and "Fc binder" and "Fc-binding protein" and "binder" are used interchangeably herein and shall be understood to relate to any protein, polypeptide, or peptide (i.e. any molecule comprising a sequence of amino acids) which can bind to an Fc domain of essentially any protein of interest, e.g. an antibody. Typically, the Fc binding polypeptides of the present invention may be derived from various sources that are either human or non-human (e.g. mammalian sources, bacteria, etc.), they have high affinity for Fc domains of various antibody isotypes, subtypes, and species (for instance IgG (as non-limiting examples in the case of IgG, IgG1, IgG2, IgG3, IgG4, IgG2a, IgG2d, and/or IgG2c), IgA, IgM, IgM, IgD, etc.), and they can optionally be fused to EV proteins. Non-limiting examples of Fc binding polypeptides in accordance with the present invention include, in addition to other Fc binding polypeptides mentioned through the present application, Protein A, Protein G, Protein A/G, Z domain, ZZ domain (two operably linked copies of the Z domain), human FCGRI, human FCGRIIA, human FCGRIIB, human FCGRIIC, human FCGRIIIA, human FCGR3B, human FCAMR, human FCERA, human FCAR, mouse FCGRI, mouse FCGRIIB, mouse FCGRIII, mouse FCGRIV, mouse FCGRn, and various combinations, derivatives, or alternatives thereof. Importantly, the Fc binding polypeptide may be fused to the exosomal polypeptide with the aid of linker comprising at least one pH sensitive cleavage site. By employing this strategy, it would be possible to capture the Fc binding polypeptide containing EVs using a chromatography matrix comprising an Fc domain, and then subsequently release the EV from the Fc domain matrix without the Fc binding polypeptide itself. This is advantageous for situations requiring the purification of exosomes which are devoid of the purification moiety, i.e. those which are not bound to any Fc binding tag. Examples of such pH sensitive sites include: Val-Val-Val-His-Asn and Val-Val-Val-His-Asn-Cys. Additional pH sensitive cleavage sites can easily be designed by a person skilled in the art. For instance, the C2 domain of Protein G can also be used as a pH sensitive site, meaning that in this case the pH sensitive domain forms part of the Fc binding polypeptide per se.

The terms "EV protein" and "EV polypeptide" and "exosomal polypeptide" and "exosomal protein" are used interchangeably herein and shall be understood to relate to any polypeptide that may be utilized to transport a polypeptide construct (which typically comprises, in addition to the EV protein, an Fc binding polypeptide) to a suitable vesicular structure, i.e. to a suitable EV. More specifically, these terms shall be understood as comprising any polypeptide that enables transporting, trafficking or shuttling of a fusion protein construct to a vesicular structure, such as an EV. Examples of such exosomal polypeptides are for instance CD9, CD53, CD63, CD81, CD54, CD50, FLOT1, FLOT2, CD49d, CD71 (also known as the transferrin receptor) and its endosomal sorting domain, i.e. the transferrin receptor endosomal sorting domain, CD133, CD138 (syndecan-1), CD235a, ALIX, ARRDC1, Syntenin-1, Syntenin-2, Lamp2b, syndecan-2, syndecan-3, syndecan-4, TSPAN8, TSPAN14, CD37, CD82, CD151, CD231, CD102, NOTCH1, NOTCH2, NOTCH3, NOTCH4, DLL1, DLL4, JAG1, JAG2, CD49d/ITGA4, ITGB5, ITGB6, ITGB7, CD11a, CD11b, CD11c, CD18/ITGB2, CD41, CD49b, CD49c, CD49e, CD51, CD61, CD104, Fc receptors, interleukin receptors, immunoglobulins, MHC-I or MHC-II components, CD2, CD3 epsilon, CD3 zeta, CD13, CD18, CD19, CD30, TSG101, CD34, CD36, CD40, CD40L, CD44, CD45, CD45RA, CD47, CD86, CD110, CD111, CD115, CD117, CD125, CD135, CD184, CD200, CD279, CD273, CD274, CD362, COL6A1, AGRN, EGFR, GAPDH, GLUR2, GLUR3, HLA-DM, HSPG2, L1CAM, LAMB1, LAMC1, LFA-1, LGALS3BP, Mac-1 alpha, Mac-1 beta, MFGE8, SLIT2, STX3, TCRA, TCRB, TCRD, TCRG, VTI1A, VTI1B, other exosomal polypeptides, and any combinations thereof, but numerous other polypeptides capable of transporting a polypeptide construct to an EV are comprised within the scope of the present invention. Typically, in many embodiments of the present invention, at least one exosomal polypeptide is fused to at least one Fc binding polypeptide, in order to form a fusion protein present in an EV. Such fusion proteins may also comprise various other components to optimize their function(s), including linkers, transmembrane domains, cytosolic domains, multimerization domains, etc.

The terms "source cell" or "EV source cell" or "parental cell" or "cell source" or "EV-producing cell" or any other similar terminology shall be understood to relate to any type of cell that is capable of producing EVs under suitable conditions, for instance in suspension culture or in adherent culture or any in other type of culturing system. Source cells as per the present invention may also include cells producing exosomes in vivo. The source cells per the present invention may be select from a wide range of cells and cell lines, for instance mesenchymal stem or stromal cells or fibroblasts (obtainable from e.g. bone marrow, adipose tissue, Wharton's jelly, perinatal tissue, tooth buds, umbilical cord blood, skin tissue, etc.), amnion cells and more specifically amnion epithelial cells optionally expressing various early markers, myeloid suppressor cells, M2 polarized macrophages, adipocytes, endothelial cells, fibroblasts, etc. Cell lines of particular interest include human umbilical cord endothelial cells (HUVECs), human embryonic kidney (HEK) cells, endothelial cell lines such as microvascular or lymphatic endothelial cells, chondrocytes, MSCs of different origin, airway or alveolar epithelial cells, fibroblasts, endothelial cells, etc. Also, immune cells such as B cells, T cells, NK cells, macrophages, monocytes, dendritic cells (DCs) are also within the scope of the present invention, and essentially any type of cell which is capable of producing EVs is also encompassed herein. Generally, EVs may be derived from essentially any cell source, be it a primary cell source or an immortalized cell line. The EV source cells may be any embryonic, fetal, and adult somatic stem cell types, including induced pluripotent stem cells (iPSCs) and other stem cells derived by any method. In highly preferred embodiments, the source cells of the present invention are of eukaryotic origin, preferably mammalian origin, and most preferably of human origin. The selection of source cells may furthermore vary depending on the intended application, for instance, when treating neurological diseases, one may contemplate to utilize as source cells e.g. neurons (e.g. primary neurons), astrocytes, oligodendrocytes, microglia, and/or neural progenitor cells, whereas in the content of the treatment of degenerative diseases cell sources such as amniotic epithelial cells, mesenchymal stromal cells, etc., may be utilized. The source cell may be either allogeneic, autologous, or even xenogeneic in nature to the patient to be treated, i.e. the cells may be from the patient himself or from an unrelated, matched or unmatched donor. In certain contexts, allogeneic cells may be preferable from a medical standpoint, as they could provide immuno-modulatory effects that may not be obtainable from autologous cells of a patient suffering from a certain indication. For instance, in the context of treating systemic, peripheral and/or neurological inflammation, allogeneic MSCs may be preferable as EVs obtainable from such cells may enable immuno-modulation via e.g. macrophage and/or neutrophil phenotypic switching (from pro-inflammatory M1 or N1 phenotypes to anti-inflammatory M2 or N2 phenotypes, respectively). Conventionally, when producing EVs for therapeutic applications the EV-producing cells are maintained in cell culture and the EVs of interest are secreted into the cell culture medium, from which they need to be purified and/or isolated using e.g. the methods of the present invention. Such culture medium may be defined or undefined, it may contain exogenous human proteins or even non-human proteins such as fetal calf (bovine) serum, and essentially any type of conventional cell culture additive. Importantly, the present invention enables the separation of EVs from such complex fluids, utilizing the interaction between the Fc binding polypeptide and the Fc domains attached to the chromatography matrix (i.e. any so called solid phase in a chromatography system).

In a first aspect, the present invention relates to a process for capturing (i.e. binding) EVs which comprise at least one Fc binding polypeptide. Said process typically comprises the steps of (i) contacting a medium comprising the EVs with a chromatography matrix comprising Fc domains, and (ii) allowing the EVs to adsorb to the Fc domains. In a further aspect, the present invention relates to a process for purifying and/or isolating from e.g. a medium comprising such Fc binding EVs, the process comprising the additional optional step of (iii) eluting the EVs by passing across the chromatography matrix a medium that releases them from the Fc domains. The principle of this process is what is known as affinity purification and/or affinity chromatography, i.e. purification of a particular target solute (in this case EVs, such as exosomes) from a complex biological fluid containing various types of solutes based on the specific interaction between a generic ligand and a generic corresponding receptor, in this case an Fc domain and a Fc binding polypeptide. The Fc domain is thus attached to a stationary phase whereas the Fc binding polypeptide is present in/on EVs which are comprised in the liquid phase, e.g. cell culture medium. The processes and methods of the present invention are easily applied to any type of cell culture medium and various cell culture medium used for both adherent and suspension cells have been tested in the affinity chromatography methods of the present invention, for instance RPMI, EMEM, DMEM, MEM, PMEM, PEM, Opti-MEM, IMDM, Advanced DMEM, McCoy's medium, medium with or without additives such serum, antibiotics, nutrients, etc.

In an advantageous embodiment, the Fc domains are part of antibodies attached to the chromatography matrix. Such antibodies are preferably attached to (so called stationary) chromatography matrix using any other part than its Fc domain, to ensure that the binding between the Fc binding polypeptide of the EVs and the Fc domain is undisturbed. In advantageous embodiments, the antibodies (i.e. the proteins comprising the Fc domain) are IgG antibodies, e.g. IgG1, IgG2, IgG3, IgG4, IgG2a, IgG2d, and/or IgG2c. However, antibodies of other isotypes may also be utilized for the present invention, as long as the constant region is capable of specifically interacting with an Fc binding polypeptide comprised in an EV. Such other isotypes may include IgA, IgM, IgM, and IgD, etc. The antibodies as per the present invention may be of human, animal, and/or synthetic origin.

In a further embodiment, the process may comprise triggering release of the EVs from the Fc domains by exposing the Fc domain-Fc binding polypeptide bond to a medium with a suitable pH. This is achieved by running the EV containing medium (i.e. the liquid phase) through e.g. a chromatography column comprising as stationary phase a chromatography matrix having attached to it Fc domains, letting the Fc binding polypeptides of the EVs adsorb to the Fc domains of the matrix, and then running a solution with a suitable pH through the chromatography column. Preferably, the pH of the solution that is intended to trigger release of the EVs from the column is below pH 8, preferably below pH 7, and even more preferably below pH 6. Both the process of capturing the EVs and the process of releasing the EVs may be repeated multiple times, e.g. anywhere from repeated once to repeated up to e.g. 500 times.

In further aspects, the chromatography matrix (also known as stationary phase in the chromatography field) may be comprised of one or more of agarose, dextran, lectin, heparin, cellulose, starch, dextran, agar, agarose, poly(meth) acrylate, polyacrylamide, polysulfone, a polyvinyl polymer, polystyrene, silica, alumina, zirconium oxide, titanium oxide, polysaccharide-mineral structure, polysaccharide-synthetic polymer, synthetic polymer-mineral structure, or any combination thereof. The matrix may be present in the form of beads, fibers, irregularly shaped particles, membranes, flat structure, porous mineral materials or essentially any type of suitable stationary phase. Naturally, the Fc domains may also be directly attached to various surfaces using chemical bonds and linkers. This could be particularly useful for methods such as e.g. surface plasmon resonance.

In further embodiments, the Fc domain may be attached to the chromatography matrix via different types of chemical and biochemical linkages and bonds. Covalent bonds between the matrix and the protein comprising the Fc domain, e.g. an antibody, may be conventional amide bonds, disulfide bonds, ether bonds, esther bonds, thio-ether bonds, thio-esther bonds, glutathione-GST interactions, streptavidin-biotin interaction, etc. The matrix may be chemically activated to facilitate binding to the Fc domain containing protein using chemical conjugation moieties such as NHS (for NHC-EDC/EDAC coupling), thiols, CNBr, epoxy, thiopropyl, primary amines, sulfhydryls, carboxylic acids, aldehydes, iodoacetyl, azlactones, CDI, maleimide, etc., as is well known to a person skilled in the art. Furthermore, various molecules may also mediate specific interaction with particular Fc domain containing proteins, such as IgG antibodies. For instance, purine-related molecules may be attached to the chromatography matrix to enable IgG binding to the matrix while maintaining the Fc domain in a free and accessible state for interaction with the Fc binding polypeptide EVs.

In preferred embodiments, the processes of the present invention are carried out in chromatography columns which comprise the chromatography matrix comprising the Fc domain and/or the Fc domain containing proteins.

In another aspect, the present invention relates to the use of a chromatography matrix for binding to EVs, wherein the chromatography matrix comprises Fc domains. As above-mentioned, the Fc domains are advantageously comprised in antibodies, e.g. IgG.

The chromatography matrix for use in capturing Fc binding EVs may consist of essentially any type of material suitable as a stationary chromatography phase. Non-limiting examples include one or more of agarose, dextran, lectin, heparin, cellulose, starch, dextran, agar, agarose, poly(meth) acrylate, polyacrylamide, polysulfone, a polyvinyl polymer, polystyrene, silica, alumina, zirconium oxide, titanium oxide, polysaccharide-mineral structure, polysaccharide-synthetic polymer, synthetic polymer-mineral structure, or any combination thereof. The matrix may be in the form of beads, fibers, irregularly shaped particles, membranes, flat structure, porous mineral materials or essentially any type of suitable stationary phase.

In a further aspect, the present invention relates to EVs comprising at least one Fc binding polypeptide, wherein said EVs are obtainable via capture and/or isolation using any of the processes of the present invention. The EVs isolated using the methods and processes herein are typically considerably more biologically active than EVs isolated using other harsher methods, as a result of less aggregation, lower degradation, no negative impact on the morphology of the EVs, etc. In comparative experiments, EVs purified using affinity chromatography as per the present invention are more efficiently internalized into target cells and exhibit higher bioactive delivery of various cargoes, e.g. siRNA and protein biologics for protein replacement therapies (e.g. delivery of the NPC1 protein into NPC1 low/deficient target cells).

In a further aspect, the present invention relates to EVs comprising at least one fusion protein, wherein the at least one fusion protein comprises at least one Fc binding polypeptide fused to at least one exosomal polypeptide. The at least one Fc binding polypeptide may preferably be selected from the group comprising Protein A, Protein G, Protein A/G, Protein L, Protein LG, Z domain, ZZ domain, human FCGRI, human FCGR2A, human FCGR2B, human FCGR2C, human FCGR3A, human FCGR3B, human FCGRB, human FCAMR, human FCERA, human FCAR, mouse FCGRI, mouse FCGRIIB, mouse FCGRIII, mouse FCGRIV, mouse FCGRn, SPH peptide, SPA peptide, SPG2, SpA mimic 1, SpA mimic 2, SpA mimic 3, SpA mimic 4, SpA mimic 5, SpA mimic 6, SpA mimic 7, SpA mimic 8, SpA mimic 9, SpA mimic 10, Fcγ mimic 1, Fcγ mimic 2, and any combination thereof. Preferably, the Fc binding polypeptide is displayed at least partially on the external surface of the EVs, to enable interaction with the Fc domain attached to the chromatography matrix.

In preferred embodiments, the at least one Fc binding polypeptide may comprise more than one Fc binding region. Further, the at least one exosomal polypeptide which may be used to transport the Fc binding polypeptide into the EVs may be selected from the group of non-limiting examples comprising CD9, CD53, CD63, CD81, CD54, CD50, FLOT1, FLOT2, CD49d, CD71, CD133, CD138, CD235a, ALIX, ARRDC1, Syntenin-1, Syntenin-2, Lamp2b, TSPAN8, TSPAN14, CD37, CD82, CD151, CD231, CD102, NOTCH1, NOTCH2, NOTCH3, NOTCH4, DLL1, DLL4, JAG1, JAG2, CD49d/ITGA4, ITGB5, ITGB6, ITGB7, CD11a, CD11b, CD11c, CD18/ITGB2, CD41, CD49b, CD49c, CD49e, CD51, CD61, CD104, Fc receptors, interleukin receptors, immunoglobulins, CD2, CD3 epsilon, CD3 zeta, CD13, CD18, CD19, CD30, CD34, CD36, CD40, CD40L, CD44, CD45, CD45RA, CD47, CD86, CD110, CD111, CD115, CD117, CD125, CD135, CD184, CD200, CD279, CD273, CD274, CD362, COL6A1, AGRN, EGFR, GAPDH, GLUR2, GLUR3, HLA-DM, HSPG2, L1CAM, LAMB1, LAMC1, LFA-1, LGALS3BP, Mac-1 alpha, Mac-1 beta, MFGE8, SLIT2, STX3, TCRA, TCRB, TCRD, TCRG, VTI1A, VTI1B, other exosomal polypeptides, and any combinations thereof. Preferably, as above-mentioned, the at least one Fc binding polypeptide is displayed on the outer surface of the EV, to enable binding to at least one but often more than one Fc domain, for instance present in an Fc domain containing protein like an antibody.

As a result of the fusion with exosomal polypeptides, the Fc binding polypeptides are efficiently displayed in very high numbers on the surface of EVs, enabling dense coating of EVs with the Fc binding polypeptides and thus high avidity of the interaction with the Fc domains attached to the chromatography matrices. For instance, the number of Fc binding polypeptides displayed on the EVs may In a further aspect, the present invention pertains to pharmaceutical compositions comprising EVs as per the present invention, and a pharmaceutically acceptable carrier. Preferably, the EVs as per the present invention are purified from cell culture medium using the processes of the present invention, to maintain their integrity, morphology, and bioactivity. The pharmaceutically acceptable excipient may be selected from the group comprising any pharmaceutically acceptable material, composition or vehicle, for instance a solid or liquid filler, a diluent, an excipient, a carrier, a solvent or an encapsulating material, which may be involved in e.g. suspending, maintaining the activity of or carrying or transporting the EV population from one organ, or portion of the body, to another organ, or portion of the body (e.g. from the blood to any tissue and/or organ and/or body part of interest).

In additional aspects, the present invention pertains to methods for producing EVs capable of binding to proteins comprising an Fc domain. Such methods may comprise the steps of: (i) introducing into an EV source cell a polynucleotide construct encoding a fusion protein comprising at least one Fc binding polypeptide and at least one exosomal polypeptide, and (ii) harvesting EVs which are secreted from EV producer cells, said EVs comprising the fusion protein of interest.

Generally, the Fc binding polypeptides as described herein may be of non-human origin, they may be obtained e.g. from bacteria, viruses, or from any non-human mammals. In another embodiment, the Fc binding polypeptides may be of human or mammal origin. In preferred embodiments of the present invention, the Fc binding polypeptides may be selected from the group comprising Protein A, Protein G, Protein A/G, Z domain, ZZ domain, Protein L, Protein LG, human FCGRI, human FCGR2A, human FCGR2B, human FCGR2C, human FCGR3A, human FCGR3B, human FCGRB, human FCAMR, human FCERA, human FCAR, mouse FCGRI, mouse FCGRIIB, mouse FCGRIII, mouse FCGRIV, mouse FCGRn, and any combination of any of the above Fc binding polypeptides. Other suitable Fc binding polypeptides, which have been obtained from e.g. phage display screening and via bioinformatics, include the Fc binding peptides SPH, SPA, SPG2, SpA mimic 1, SpA mimic 2, SpA mimic 3, SpA mimic 4, SpA mimic 5, SpA mimic 6, SpA mimic 7, SpA mimic 8, SpA mimic 9, SpA mimic 10, Fcγ mimic 1, and Fcγ mimic 2, and any combination or derivative thereof. The selection of the most suitable Fc binding polypeptide for a particular construct depends heavily on the desired binding characteristics, the affinity, the orientation of the Fc binding polypeptide when fused to an exosomal polypeptide, and various other factors.

Protein A/G is a recombinant genetically engineered protein comprised of 7 Fc-binding domains EDABC-C1C3, with the Protein A part being obtained from *Staphylococcus aureus* segments E, D, A, B and C, and the Protein G part from *Streptococcus* segments C1 and C3. Advantageously, Protein A/G has a broader binding capacity than either Protein A or Protein G alone and it has a broad binding affinity for antibodies from various species. Protein A/G binds to various human, mouse and rat IgG subclasses such as the human IgG1, IgG2, IgG3, IgG4; mouse IgG2a, IgG2b, IgG3 and rat IgG2a, IgG2c. In addition, Protein A/G binds to total IgG from cow, goat, sheep, horse, rabbit, guinea pig, pig, dog and cat. Protein A/G has been engineered to remove the cell wall-binding region, the cell membrane-binding region and albumin-binding region to enable strong binding to the Fc domain of a protein of interest attached to a stationary phase. Thus, in advantageous embodiments as per the present invention, the Fc binding polypeptide may comprise more than one Fc binding region, as is the case with Protein A, Protein G, and Protein A/G. In an alternative embodiment, the Fc binding polypeptide may be multiplied in order to enable binding to more than one copy of an antibody of interest. For instance, the short Z domain Fc binder may be included in a fusion protein with an exosomal polypeptide in more than one copy, through an operational linkage allowing for binding to more than one Fc domain. This way it is possible to enable binding to multiple Fc domains comprised in the chromatography matrix and other Fc domain-containing proteins not only between separate fusion proteins but also within one single fusion protein. For instance, when Fc binding polypeptides are introduced into exosomal polypeptides belonging to the tetraspanin family (such as CD63) it may be advantageous to insert one Fc binding polypeptide in one loop of CD63 and another Fc binding polypeptide (which can be the same or different) in another loop of the protein. Some non-limiting examples of fusion proteins between Fc binding polypeptides and exosomal polypeptides as per the present invention can be described schematically as follows (the below notation is not to be construed as illustrating any C and/or N terminal direction, it is merely meant for illustrative purposes):

Exosomal polypeptide-Fc binding polypeptide-Fc binding polypeptide

Exosomal polypeptide domain-Fc binding polypeptide-Exosomal polypeptide domain-Fc binding polypeptide Exosomal polypeptide domain-Fc binding polypeptide A-Exosomal polypeptide domain-Fc binding polypeptide B In preferred embodiments, the at least one Fc binding polypeptide is linked to the exosomal polypeptide via a linker comprising a pH sensitive cleavage site. The presence of such a cleavage site comprised in the fusion protein comprising the exosomal polypeptide and the Fc binding polypeptides enables not only affinity capture of the Fc binding EVs but also removal of the entire Fc binding polypeptide from the EV itself, by merely changing the pH. This can be done as part of the elution process from the chromatography matrix and/or in a separate step. Inserting the cleavage site in between the exosomal polypeptide and the Fc binding polypeptide is advantageous, since it allows for a clean cut removal of the EVs from both the matrix and the Fc binding polypeptide.

In advantageous embodiments, the EVs according to the present invention may comprise a substantial plurality of Fc binding polypeptides, to enable binding to the Fc domains forming part of the chromatography matrix. For instance, when using a highly expressed EV protein such as CD63 or CD81 or syntenin one can achieve very dense coating of the surface of EVs. Thus, EVs of the present invention may comprise at least 10 fusion polypeptides proteins comprising an Fc binding polypeptide, or even more preferably at least 20, 50, or above 100 fusion polypeptides. Such proteins may be copies of the same fusion polypeptide or multiple copies of different polypeptides.

In further aspects, the methods and processes of the present invention may also comprise exposing the EV source cells to serum starvation, hypoxia, bafilomycin, or cytokines such as TNF-alpha and/or IFN-gamma, in order to influence the yield or properties of the resulting EVs. The EV production scale and timeline will be heavily dependent on the EV-producing cell or cell line and may thus be adapted accordingly by a person skilled in the art. The methods as per the present invention may further comprise additional EV purification step(s), which may be carried out prior to the affinity capture step(s) of the present invention. For instance, EVs may be purified using methods selected from a group of techniques comprising liquid chromatography (LC), high-performance liquid chromatography (HPLC), bead-eluate chromatography, spin filtration, tangential flow filtration (TFF), hollow fiber filtration, centrifugation, immunoprecipitation, flow field fractionation, dialysis, microfluidic-based separation, etc., or any combination thereof. In an advantageous embodiment, the purification of the EVs is carried out using a sequential combination of filtration (preferably ultrafiltration (UF) or tangential flow filtration (TFF)) and affinity chromatography, optionally also including size exclusion liquid chromatography (LC) or bead-eluate LC. Combining purification steps normally enhances the purity of the resulting samples and, in turn leading to superior therapeutic activity.

Importantly, as above-mentioned, the affinity purification of Fc binding EVs may be run multiple times, essentially indefinitely but at least anywhere between 2 and 500 times. As is exemplified herein, sequential purification of Fc binding EVs enable drug loading between purification steps. For instance, Fc binding EVs may be purified directly from the conditioned medium of the EV-producing cell source, followed by a drug loading step, and yet another round of purification. The Fc binding EVs of the present invention are highly suitable as delivery vehicles for antibodies and adhering to the above step-by-step purification protocol enables highly efficient loading and purification of antibody-carrying EVs. Schematically, this can be illustrated as follows:

Secretion of EVs into cell culture medium by EV-producing cells

Affinity purification of EVs using the processes and methods of the present invention Drug loading (for instance, loading of antibodies onto the surface of EVs)

Affinity purification of EVs using the processes and methods of the present invention The present invention also relates to cosmetic applications of EVs. Thus, the present invention may pertain to skin care products such as creams, lotions, gels, emulsions, ointments, pastes, powders, liniments, sunscreens, shampoos, etc., comprising a suitable EV, in order to improve and/or alleviate symptoms and problems such as dry skin, wrinkles, folds, ridges, and/or skin creases. In one embodiment, EVs (carrying a fusion protein bound to e.g. an antibody of interest) are obtained from a suitable EV-producing cell source with regenerative properties (for instance an MSC or an amnion-derived cell source) are comprised in a cosmetic cream, lotion, or gel for use in the cosmetic or therapeutic alleviation of wrinkles, lines, folds, ridges and/or skin creases.

In yet another aspect, the present invention relates to EVs as per the present invention for use in medicine. Naturally, when EVs are used in medicine, it is in fact normally a population of EVs that is being used. The dose of EVs administered to a patient will depend the disease or the symptoms to be treated or alleviated, the administration route, the pharmacological action of the therapeutics included in and/or delivered by the EVs themselves, the inherent properties of the EVs, the presence of any targeting entities, as well as various other parameters of relevance known to a skilled person.

The EVs and the EV populations as per the present invention may thus be used for prophylactic and/or therapeutic purposes, e.g. for use in the prophylaxis and/or treatment and/or alleviation of various diseases and disorders. A non-limiting sample of diseases wherein the EVs as per the present invention may be applied comprises Crohn's disease, ulcerative colitis, ankylosing spondylitis, rheumatoid arthritis, multiple sclerosis, systemic lupus erythematosus, sarcoidosis, idiopathic pulmonary fibrosis, psoriasis, tumor necrosis factor (TNF) receptor-associated periodic syndrome (TRAPS), deficiency of the interleukin-1 receptor antagonist (DIRA), endometriosis, autoimmune hepatitis, scleroderma, myositis, stroke, acute spinal cord injury, vasculitis, Guillain-Barré syndrome, acute myocardial infarction, ARDS, sepsis, meningitis, encephalitis, liver failure, non-alcoholic steatohepatitis (NASH), non-alcoholic fatty liver disease (NAFLD), kidney failure, heart failure or any acute or chronic organ failure and the associated underlying etiology, graft-vs-host disease, Duchenne muscular dystrophy and other muscular dystrophies, lysosomal storage diseases such as Gaucher disease, Fabry's disease, MPS I, II (Hunter syndrome), and III, Niemann-Pick disease, Niemann-Pick disease type C, Danon disease, Pompe disease, etc., neurodegenerative diseases including Alzheimer's disease, Parkinson's disease, Huntington's disease and other trinucleotide repeat-related diseases, dementia, ALS, cancer-induced cachexia, anorexia, diabetes mellitus type 2, and various cancers. Virtually all types of cancer are relevant disease targets for the present invention, for instance, Acute lymphoblastic leukemia (ALL), Acute myeloid leukemia, Adrenocortical carcinoma, AIDS-related cancers, AIDS-related lymphoma, Anal cancer, Appendix cancer, Astrocytoma, cerebellar or cerebral, Basal-cell carcinoma, Bile duct cancer, Bladder cancer, Bone tumor, Brainstem glioma, Brain cancer, Brain tumor (cerebellar astrocytoma, cerebral astrocytoma/malignant glioma, ependymoma, medulloblastoma, supratentorial primitive neuroectodermal tumors, visual pathway and hypothalamic glioma), Breast cancer, Bronchial adenomas/carcinoids, Burkitt's lymphoma, Carcinoid tumor (childhood, gastrointestinal), Carcinoma of unknown primary, Central nervous system lymphoma, Cerebellar astrocytoma/Malignant glioma, Cervical cancer, Chronic lymphocytic leukemia, Chronic myelogenous leukemia, Chronic myeloproliferative disorders, Colon Cancer, Cutaneous T-cell lymphoma, Desmoplastic small round cell tumor, Endometrial cancer, Ependymoma, Esophageal cancer, Extracranial germ cell tumor, Extragonadal Germ cell tumor, Extrahepatic bile duct cancer, Eye Cancer (Intraocular melanoma, Retinoblastoma), Gallbladder cancer, Gastric (Stomach) cancer, Gastrointestinal Carcinoid Tumor, Gastrointestinal stromal tumor (GIST), Germ cell tumor (extracranial, extragonadal, or ovarian), Gestational trophoblastic tumor, Glioma (glioma of the brain stem, Cerebral Astrocytoma, Visual Pathway and Hypothalamic glioma), Gastric carcinoid, Hairy cell leukemia, Head and neck cancer, Heart cancer, Hepatocellular (liver) cancer, Hodgkin lymphoma, Hypopharyngeal cancer, Intraocular Melanoma, Islet Cell Carcinoma (Endocrine Pancreas), Kaposi sarcoma, Kidney cancer (renal cell cancer), Laryngeal Cancer, Leukemias ((acute lymphoblastic (also called acute lymphocytic leukemia), acute myeloid (also called acute myelogenous leukemia), chronic lymphocytic (also called chronic lymphocytic leukemia), chronic myelogenous (also called chronic myeloid leukemia), hairy cell leukemia)), Lip and Oral, Cavity Cancer, Liposarcoma, Liver Cancer (Primary), Lung Cancer (Non-Small Cell, Small Cell), Lymphomas, AIDS-related lymphoma, Burkitt lymphoma, cutaneous T-Cell lymphoma, Hodgkin lymphoma, Non-Hodgkin, Medulloblastoma, Merkel Cell Carcinoma, Mesothelioma, Metastatic Squamous Neck Cancer with Occult Primary, Mouth Cancer, Multiple Endocrine Neoplasia Syndrome, Multiple Myeloma/Plasma Cell Neoplasm, Mycosis Fungoides, Myelodysplastic/Myeloproliferative Diseases, Myelogenous Leukemia, Chronic Myeloid Leukemia (Acute, Chronic), Myeloma, Nasal cavity and paranasal sinus cancer, Nasopharyngeal carcinoma, Neuroblastoma, Oral Cancer, Oropharyngeal cancer, Osteosarcoma/malignant fibrous histiocytoma of bone, Ovarian cancer, Ovarian epithelial cancer (Surface epithelial-stromal tumor), Ovarian germ cell tumor, Ovarian low malignant potential tumor, Pancreatic cancer, Pancreatic islet cell cancer, Parathyroid cancer, Penile cancer, Pharyngeal cancer, Pheochromocytoma, Pineal astrocytoma, Pineal germinoma, Pineoblastoma and supratentorial primitive neuroectodermal tumors, Pituitary adenoma, Pleuropulmonary blastoma, Prostate cancer, Rectal cancer, Renal cell carcinoma (kidney cancer), Retinoblastoma, Rhabdomyosarcoma, Salivary gland cancer, Sarcoma (Ewing family of tumors sarcoma, Kaposi sarcoma, soft tissue sarcoma, uterine sarcoma), Sézary syndrome, Skin cancer (nonmelanoma, melanoma), Small intestine cancer, Squamous cell, Squamous neck cancer, Stomach cancer, Supratentorial primitive neuroectodermal tumor, Testicular cancer, Throat cancer, Thymoma and Thymic carcinoma, Thyroid cancer, Transitional cell cancer of the renal pelvis and ureter, Urethral cancer, Uterine cancer, Uterine sarcoma, Vaginal cancer, Vulvar cancer, Waldenström macroglobulinemia, and/or Wilm's tumor.

The EVs as per the present invention may be administered to a human or animal subject via various different administration routes, for instance auricular (otic), buccal, conjunctival, cutaneous, dental, electro-osmosis, endocervical, endosinusial, endotracheal, enteral, epidural, extra-amniotic, extracorporeal, hemodialysis, infiltration, interstitial, intraabdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal (dental), intracoronary, intracorporus cavernosum, intradermal, intradiscal, intraductal, intraduodenal, intradural, intraepidermal, intraesophageal, intragastric, intragingival, intrailleal, intralesional, intraluminal, intralymphatic, intramedullary, intrameningeal, intramuscular, intraocular, intranasal, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intravenous bolus, intravenous drip, intraventricular, intravesical, intravitreal, iontophoresis, irrigation, laryngeal, nasal, nasogastric, occlusive dressing technique, ophthalmic, oral, oropharyngeal, other, parenteral, percutaneous, periarticular, peridural, perineural, periodontal, rectal, respiratory (inhalation), retrobulbar, soft tissue, subarachnoid, subconjunctival, subcutaneous, sublingual, submucosal, topical, transdermal, transmucosal, transplacental, transtracheal, transtympanic, ureteral, urethral, and/or vaginal administration, and/or any combination of the above administration routes, which typically depends on the disease to be treated and/or the characteristics of the EV population as such.

It shall be understood that the above described exemplifying aspects, embodiments, alternatives, and variants can be modified without departing from the scope of the invention. The invention will now be further exemplified with the enclosed examples, which naturally also can be modified considerably without departing from the scope and the gist of the invention.

Experimentals

Materials and Methods

Construct design and cloning: Various fusion proteins comprising at least one exosomal polypeptide and at least one Fc binding polypeptide have been constructed, cloned into vectors and produced in several different EV-producing cell sources. ORFs were typically generated by synthesis and cloned into the mammalian expression vector pSF-CAG-Amp. Briefly, synthesized DNA and vector plasmid were digested with enzymes NotI and SalI as per manufacturers instruction (NEB). Restricted, purified DNA fragments were ligated together using T4 ligase as per manufacturers instruction (NEB). Successful ligation events were selected for by bacterial transformation on ampicillin-supplemented plates. Plasmid for transfection was generated by 'maxi-prep', as per manufacturers instruction.

Cell Culture and Transfection

Depending on the experimental design and assays, in certain cases, non-viral transient transfection and exosome production was carried out in conventional 2D cell culture, whereas in other cases virus-mediated transduction was employed to create stable cell lines, which were typically cultured in bioreactors of different type. For conciseness, only a few examples are mentioned herein.

HEK293T cells were typically seeded into 15 cm dishes ($9 \times 10^6$ cells per dish) and left overnight in serum-containing DMEM as recommended by ATCC. The following day the cells were transiently transfected with lipoplexed DNA added directly onto cells. Briefly, DNA and polyethylene-imine (PEI) were separately incubated in OptiMEM for 5 minutes before combining together for 20 minutes at room temperature. Lipoplexed DNA and cells were co-incubated for 6 hours following which conditioned culture media was changed to OptiMEM for 48 hours. Other cells and cell lines that were evaluated in dishes, flasks and other cell culture vessels included bone marrow-derived mesenchymal stromal cells (BM-MSCs) and Wharton's jelly-derived MSCs (WJ-MSCs), amnion cells, fibroblasts, various endothelial and epithelial cells, as well as various immune cells and cell lines.

In the case of viral transduction and creation of stable cell lines for various combinations of fusion proteins and Fc containing proteins of interest, cell sources such as BM-MSCs, WJ-MSC, fibroblasts, amniotic tissue-derived cells, fibroblasts, various endothelial and epithelial cells, were virus-transduced, typically using lentivirus (LV). Typically, 24 hours before infection, 100.000 cells (e.g. fibroblasts, MSCs, etc.) or 200.000 cells (e.g. HEK293T) are plated in a 6-well plate. 2 uL of LV and optionally Polybrene (or hexadimethrine bromide, final concentration on the well of 8 ug/mL) are added, and 24 hours post transduction the cell medium of transduced cells is changed to fresh complete media. At 72 hours post transduction, puromycin selection (4-6 µg/ml) is performed, normally for 7 days followed by analysis of stable expression of the fusion protein construct comprising the exosomal polypeptide and the Fc binding polypeptide.

Stable cells were cultured in either 2D culture or in bioreactors, typically hollow-fiber bioreactors or stir-rank bioreactors, and conditioned media was subsequently harvested for exosome preparation. Various preparation and purification steps were carried out. The standard workflow comprises the steps of pre-clearing of the supernatant, filtration-based concentration, chromatography-based removal of protein contaminants, and optional formulation of the resultant exosome composition in a suitable buffer for in vitro and/or in vivo assays.

Assays and Analytics

Western blot is a highly convenient analytical method to evaluate the enrichment of fusion proteins in EVs. Briefly, SDS-PAGE was performed according to manufacturer's instruction (Invitrogen, Novex PAGE 4-12% gels), whereby $1 \times 10^{10}$ exosomes and 20 ug cell lysate were loaded per well. Proteins from the SDS-PAGE gel were transferred to PVDF membrane according to manufacturer's instruction (Immobilon, Invitrogen). Membranes were blocked in Odyssey blocking buffer (Licor) and probed with antibodies against the Fc binding polypeptide and/or the exosomal protein according to supplier's instruction (Primary antibodies—Abcam, Secondary antibodies—Licor). Molecular probes visualized at 680 and 800 nm wavelengths.

For EV size determination, nanoparticle tracking analysis (NTA) was performed with a NanoSight instrument equipped with analytical software. For all recordings, we used a camera level of 13 or 15 and automatic function for all post-acquisition settings. Electron microscopy and fluorescence microscopy were frequently used to understand intracellular location and release and to quantitate and analyze EVs.

Example 1: Binding of EVs Comprising Fc Binding Polypeptides to IgG as a Proof of Principle of Binding to Fc Domain Containing Chromatography Matrices EVs were isolated from the conditioned medium from engineered HEK293T cells (control versus Fc-binding construct that stably express syntenin coupled to a transmembrane domain from the TNF receptor fused to Protein A) using tangential flow filtration with 300 kd hollow fiber columns, followed by ultrafiltration using 10 kd spin filters for concentration. The binding capacity for IgG by the Fc-binding EVs were then assessed using electron microscopy and flow cytometry.

Figure 2:
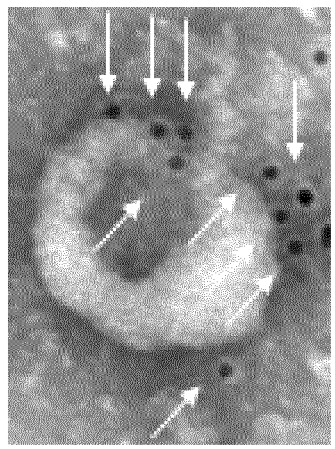
FIG. 2. Electron microscopy pictures of EVs comprising Fc binding polypeptides (A) are decorated with nanogold labeled antibodies (i.e. Fc containing proteins), whereas control EVs (B), which lack Fc binding polypeptides, do not have any antibodies bound to their surfaces.
Figure 2:
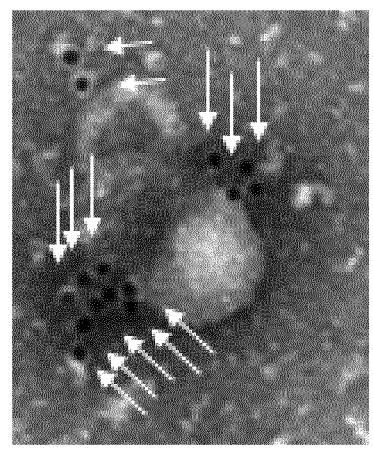
Figure 2:
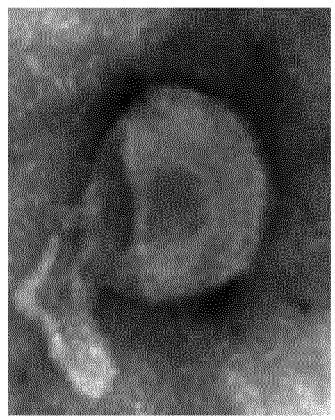
Figure 2:
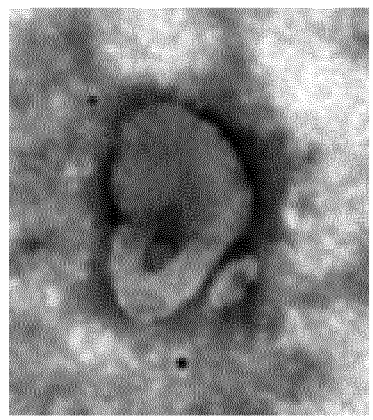
Figure 3A:
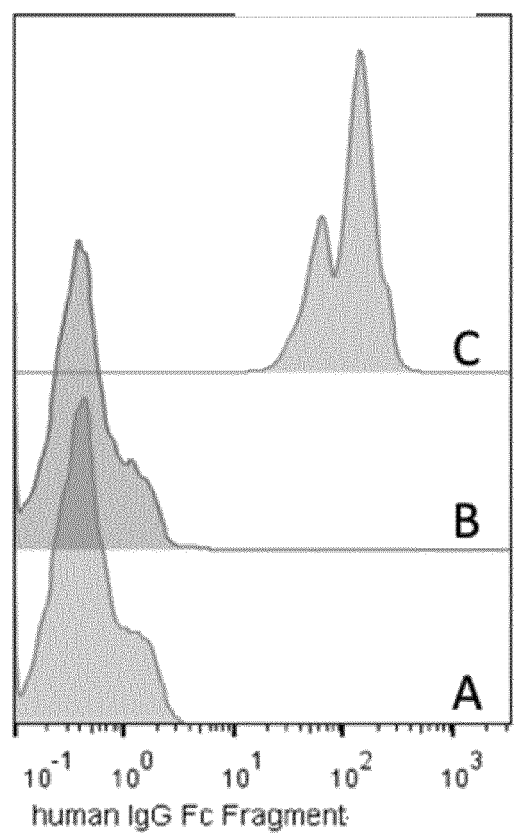
FIG. 3. Flow cytometry data showing that EVs comprising Fc binding polypeptides bind Fc containing proteins of interest (in this case illustrated with human IgG, which is commonly used in liquid chromatography purification columns). The binding is very efficient to all bead populations included in the kit, including the unspecific/isotype/negative control bead populations FIG. 4. Antibody-coated EVs purified twice using affinity chromatography delivered an intracellular anti-NFkB antibody at higher bioactivity than UF-SEC purified antibody-EVs, shown by a significant difference in downregulation of the signaling pathway.
Figure 3A:
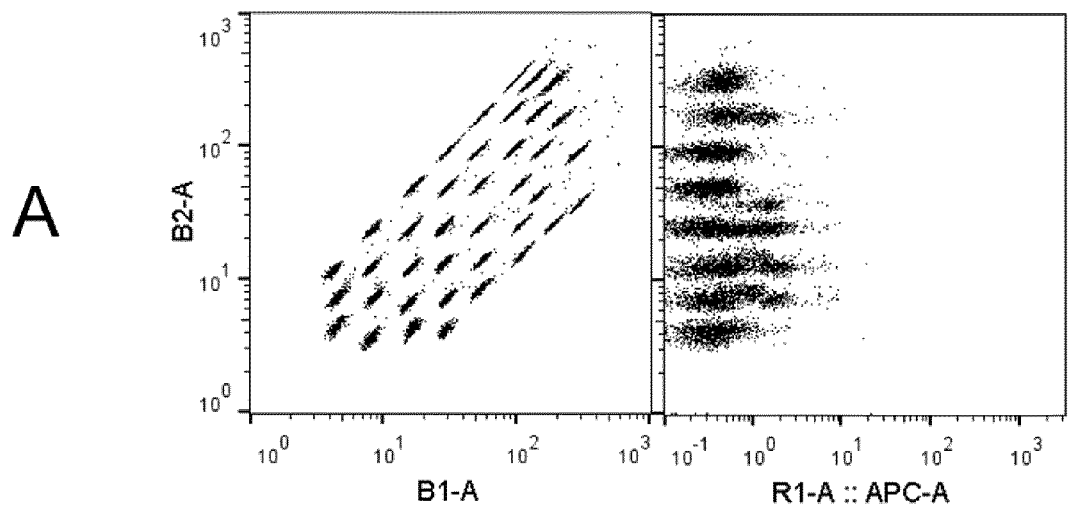
Figure 3B:
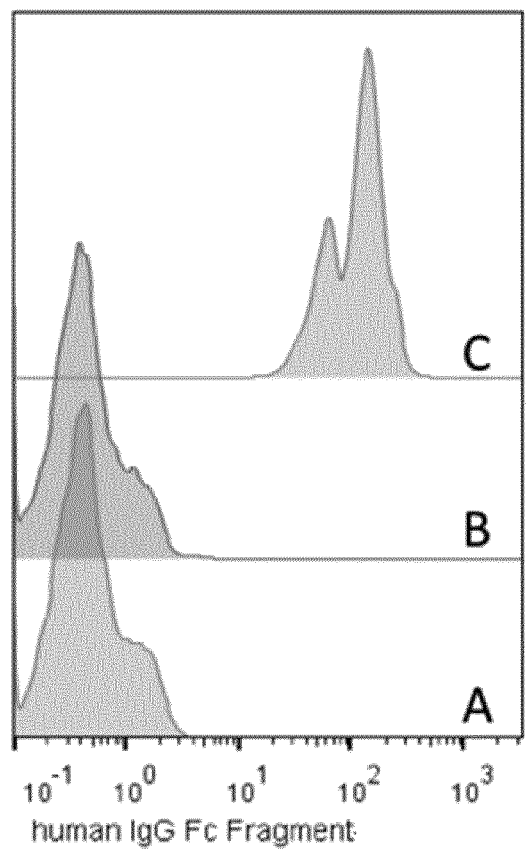
Figure 3B:
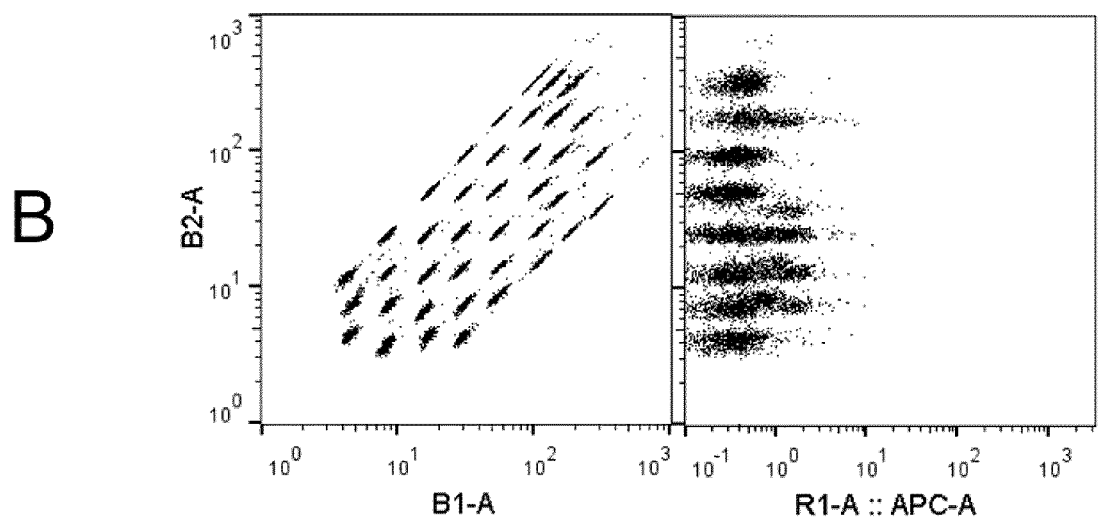
Figure 3C:
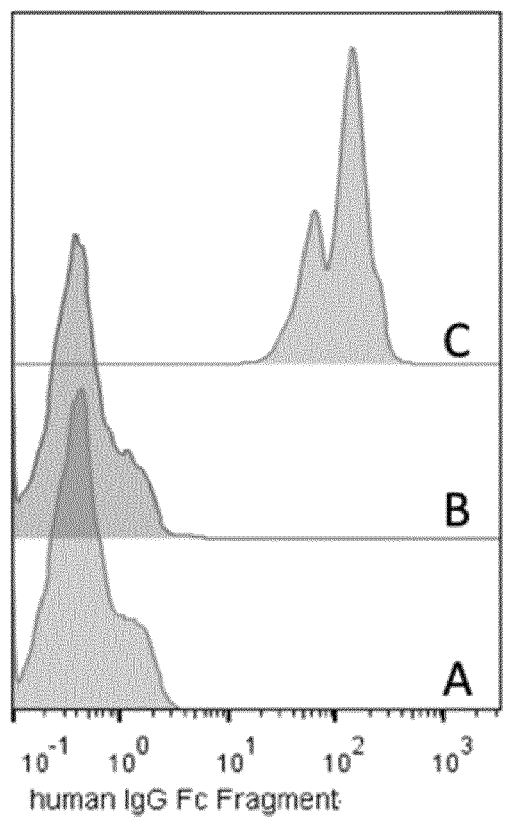
Figure 3C:
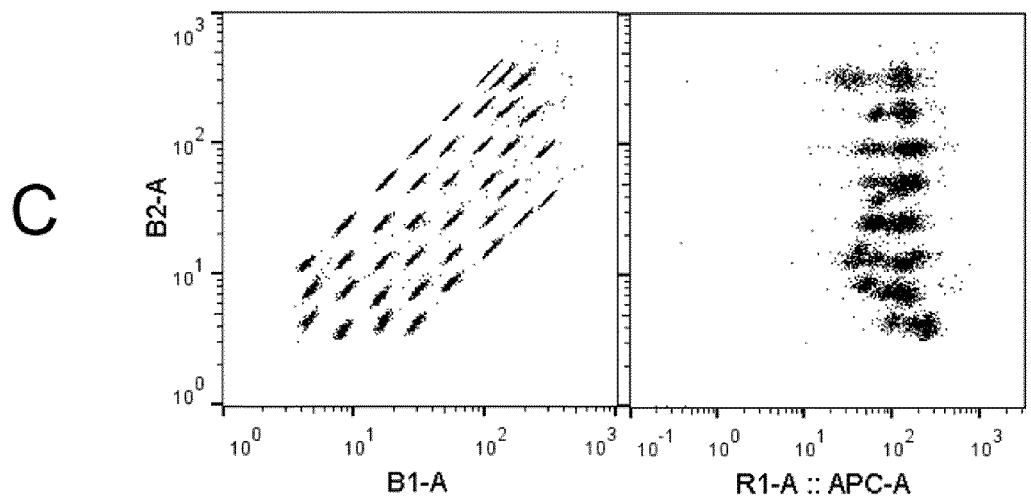
Figure 4:
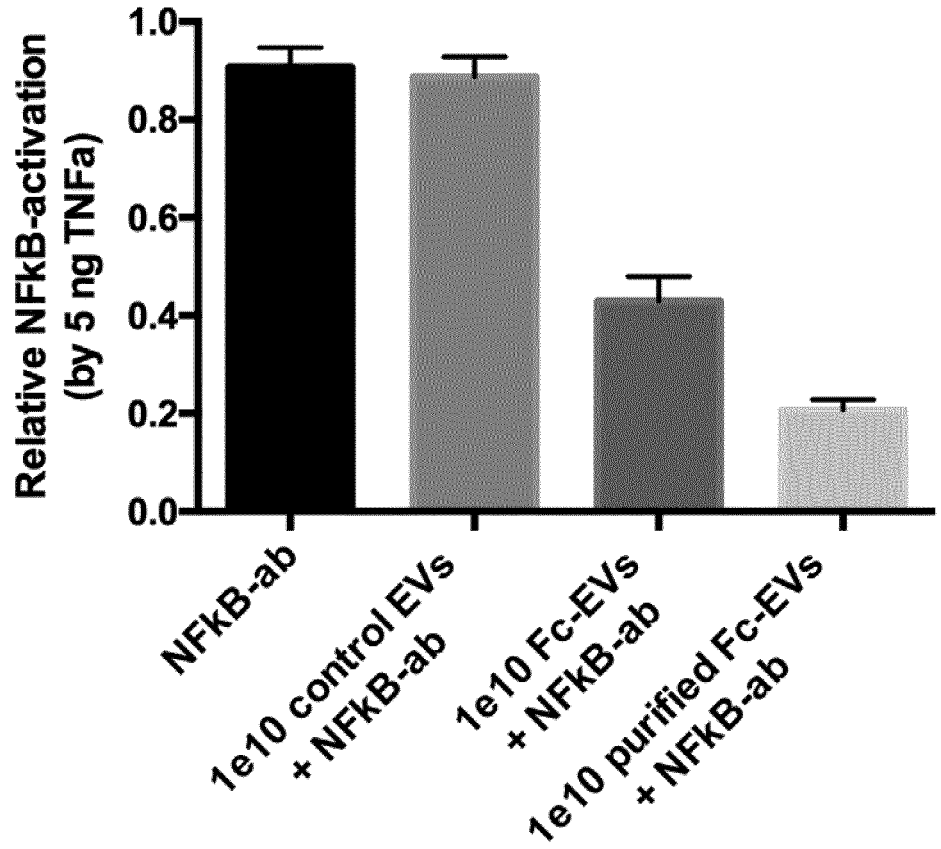

For electron microscopy, $1 \times 10^9$ EVs were incubated with Rabbit anti-goat 10 nm antibody conjugated with gold Nanoparticles for 2 h at 37° C. As shown in FIG. 2, Fc-binding EVs (A) are decorated with nanogold labeled antibodies (i.e. Fc containing proteins), whereas control EVs (B) do not have any antibodies bound.

For flow cytometry, $1 \times 10^8$ EVs were incubated overnight on an orbital shaker at 450 rpm for 16 hours in 120 µl PBS with 15 µl antibody-coated capture beads from the MACSPlex Exosome Kit, human (Miltenyi Biotec, Order no 130-108-813). After washing, 3 µg of AlexaFluor647-conjugated human IgG Fc fragments (Jackson Laboratories, Catalogue 009-600-008) were added to controls without EVs (A), control EVs (B), or Fc-binding EVs (C). After a 1 hour incubation at room temperature, unbound Fc fragments were washed away and samples were analyzed via flow cytometry. In FIG. 3 respective left dotplots show hard-dyed capture bead populations using B1-A (Excitation: 488 nm, Emission Filter: 500-550 nm; Area) versus B2-A (Excitation: 488 nm, Emission Filter: 565-605 nm, Area) parameters. Respective right plots show R1-A (Excitation: 635 nm, Emission Filter: 655-730 nm, Area) versus B2-A parameters, demonstrating binding of AlexaFluor647 labeled Fc-Fragments to EVs which have bound to the capture beads only in (C). FIG. 3 shows that the Fc-binding EVs bind both to AlexaFluor647-labelled Fc fragments (human IgG) and very efficiently also to the Fc domains of all 39 different antibodies which are coated on all capture bead populations by the manufacturer included in the kit, including the two negative control bead populations.

Example 2: Purification of EVs Comprising Fc Binding Polypeptides Using Fc Domain Affinity Chromatography EV-containing media was collected from genetically engineered MSCs grown in a hollow-fibre bioreactor. The MSCs secreted exosomes comprising a fusion polypeptide between CD63 and the Z domain, wherein the Z domain was inserted into the first and second loop of the CD63 protein.

The cell medium obtained from the bioreactor was loaded onto an IgG column (IgG Sepharose Fast Flow 6, GE Healthcare Life Sciences), connected to an ÄKTAprime plus or ÄKTA Pure 25 chromatography system (GE Healthcare Life Sciences). The IgG Sepharose Fast Flow 6 is based on a rigid Sepharose 6 Fast Flow matrix, with human IgG covalently coupled to it. This allows for flow rates that can be relatively high, to enable quick and efficient purification target solutes that bind to IgG, and more specifically the Fc domain of IgG. The agarose matrix is a highly cross-linked 6% agarose matrix, which can bind at least 2 g Protein A/ml medium.

Flow rate settings for column equilibration, sample loading and column cleaning in place procedure were chosen according to the manufacturer's instructions. An elution buffer comprising 0.5 M HAc, with a pH of 3-6, or a buffer comprising 0.1 M glycine-HCl, pH 3.0, were utilized to elute the IgG bound Fc binding EVs. Competitive elution using the ZZ domain was also tested separately. The sample was collected according to the UV absorbance chromatogram and concentrated using an Amicon Ultra-15 10 kDa molecular weight cut-off spin-filter (Millipore) to a final volume of 100 µl and stored at −80° C. for further downstream analysis, using flow cytometry, electron microscopy, and bioactivity assays.

Example 3: Comparing Bioactivity of UF-SEC and Affinity Chromatography Purified EVs EVs were isolated from the conditioned medium of MSCs (stably expressing either CD81-GFP or CD81-z-domain) using ultrafiltration and size exclusion chromatography (UF-SEC) or IgG-based affinity liquid chromatography. In order to investigate any differences in intracellular delivery of Abs, 1e10 EVs were incubated for 2 hours at room temperature with 2 µg anti-NFkB antibodies (anti-NFkB-Ab) and excess mAb was cleaned away using the same IgG-based affinity purification step. Elution conditions for both the EV purification run and the EV-Ab purification run was: 0.5 M HAc, pH 3-6, but 0.1 M glycine-HCl, pH 3.0 has also been evaluated. Competitive elution using the ZZ domain was also tested separately.

A reporter cell line, HEK cells stably expressing NFkB-luciferase, were treated with 5 ng/ml hTNF-alpha and the EV-Ab-mix (with EVs obtained from either UF-SEC or affinity chromatography). After 6 hours of treatment luciferase activity was measured. Antibody-coated EVs purified using affinity chromatography delivered the intracellular anti-NFkB antibody at higher bioactivity, shown by a significant difference in downregulation of the signaling pathway as compared to UF-SEC purified antibody-coated EVs.

The invention claimed is:

1. A process for capturing at least one exosome comprising at least one fusion protein, wherein the at least one fusion protein comprises at least one Fc binding polypeptide and at least one exosomal polypeptide, and wherein the Fc binding polypeptide is displayed on the outer surface of the exosome, the process comprising:
(i) introducing into a population of exosome source cells a polynucleotide construct encoding the fusion protein;
(ii) culturing the population of exosome source cells in a cell culture medium under conditions sufficient to produce at least one exosome, thereby producing a composition comprising the cell culture medium and at least one exosome; and
(iii) contacting the composition produced in step (ii) with a chromatography matrix comprising Fc domains, thereby capturing the at least one exosome.

2. The process of claim 1, wherein the Fc domains are part of antibodies attached to the chromatography matrix.

3. The process of claim 2, wherein the antibodies are IgG antibodies.

4. The process of claim 2, wherein the antibodies are of human, animal, or synthetic origin.

5. A process for isolating at least one exosome comprising at least one fusion protein, wherein the at least one fusion protein comprises at least one Fc binding polypeptide and at least one exosomal polypeptide, and wherein the Fc binding polypeptide is displayed on the outer surface of the exosome, the process comprising:
(i) introducing into a population of exosome source cells a polynucleotide construct encoding the fusion protein;
(ii) culturing the population of exosome source cells in a cell culture medium under conditions sufficient to produce at least one exosome, thereby producing a composition comprising the cell culture medium and at least one exosome;
(iii) contacting the composition produced in step (ii) with a chromatography matrix comprising Fc domains; and
(iv) eluting the at least one exosome from the chromatography matrix.

6. The process of claim 5, wherein release of the at least one exosome from the Fc domains is triggered by a pH below 8.

7. The process of claim 1 or claim 5, wherein the at least one exosomal polypeptide is selected from the group consisting of CD9, CD53, CD63, CD81, CD54, CD50, FLOT1, FLOT2, CD49d, CD71, CD133, CD138, CD235a, ALIX, ARRDC1, Syntenin-1, Syntenin-2, Lamp2b, TSPAN8, TSPAN14, CD37, CD82, CD151, CD231, CD102, NOTCH1, NOTCH2, NOTCH3, NOTCH4, DLL1, DLL4, JAG1, JAG2, CD49d/ITGA4, ITGB5, ITGB6, ITGB7, CD11a, CD11b, CD11c, CD18/ITGB2, CD41, CD49b, CD49c, CD49e, CD51, CD61, CD104, Fc receptors, interleukin receptors, immunoglobulins, CD2, CD3 epsilon, CD3 zeta, CD13, CD18, CD19, CD30, CD34, CD36, CD40, CD40L, CD44, CD45, CD45RA, CD47, CD86, CD110, CD111, CD115, CD117, CD125, CD135, CD184, CD200, CD279, CD273, CD274, CD362, COL6A1, AGRN, EGFR, GAPDH, GLUR2, GLUR3, HLA-DM, HSPG2, L1CAM, LAMB1, LAMC1, LFA-1, LGALS3BP, Mac-1 alpha, Mac-1 beta, MFGE8, SLIT2, STX3, TCRA, TCRB, TCRD, TCRG, VTI1A, and VTI1B.

8. The process of claim 1 or claim 5, wherein the chromatography matrix comprises one or more of agarose, dextran, lectin, heparin, cellulose, a starch, dextran, agar, agarose, a poly(meth)acrylate, a polyacrylamide, a polysulfone, a polyvinyl polymer, polystyrene, silica, alumina, zirconium oxide, titanium oxide, polysaccharide-mineral structure, a polysaccharide-synthetic polymer, or a synthetic polymer-mineral structure.

9. The process of claim 1 or claim 5, wherein the chromatography matrix is in the form of beads, fibers, irregularly shaped particles, membranes, flat structure or porous mineral materials.

10. The process of claim 1 or claim 5, wherein the process is carried out in a chromatography column comprising the chromatography matrix.

* * * * *